US012806083B2

(12) United States Patent
Borkovetz et al.

(10) Patent No.: US 12,806,083 B2
(45) Date of Patent: Nov. 24, 2026

(54) ABSORBENT ARTICLE

(71) Applicant: Kimberly-Clark Worldwide, Inc., Neenah, WI (US)

(72) Inventors: Lindsay Borkovetz, Hortonville, WI (US); Matthew R. Van Hout, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 965 days.

(21) Appl. No.: 17/753,985

(22) PCT Filed: Dec. 16, 2019

(86) PCT No.: PCT/US2019/066514
§ 371 (c)(1),
(2) Date: Mar. 21, 2022

(87) PCT Pub. No.: WO2021/126149
PCT Pub. Date: Jun. 24, 2021

(65) Prior Publication Data
US 2022/0370260 A1 Nov. 24, 2022

(51) Int. Cl.
*A61F 13/49* (2006.01)

(52) U.S. Cl.
CPC .... *A61F 13/4902* (2013.01); *A61F 13/49012* (2013.01); *A61F 2013/49025* (2013.01); *A61F 2013/49036* (2013.01)

(58) Field of Classification Search
CPC ............ A61F 13/4902; A61F 13/49012; A61F 2013/49025; A61F 2013/49036
See application file for complete search history.

(56) References Cited

U.S. PATENT DOCUMENTS 6,482,191 B1 11/2002 Roe et al.
8,257,332 B2 9/2012 Tsang et al.
(Continued)

FOREIGN PATENT DOCUMENTS

CN 101795653 A 8/2010
CN 103263321 A 8/2013
(Continued)

OTHER PUBLICATIONS

Fameccanica, "Adult diaper, pull-on and underpad machines", Fameccanica.com, https://www.fameccanica.com/adultincontinencemachines.
(Continued)

*Primary Examiner* — Rebecca E Eisenberg
*Assistant Examiner* — Kate Elizabeth Strachan
(74) *Attorney, Agent, or Firm* — KIMBERLY-CLARK WORLDWIDE, INC.

(57) ABSTRACT

An absorbent article, such as, a garment-like absorbent article, can have a front region, a back region, and a crotch region extending between and interconnecting the front region and the back region. Each of the front region and the back region can have an elastic material. The absorbent article can have an absorbent core wherein a portion of the absorbent core can be located in the crotch region, a portion of the absorbent core can be located in a portion of the front region, and a portion of the absorbent core can be located in a portion of the back region. Within each of the front region and the back region, an overlapping region can exist where the absorbent core is in an overlapping configuration with the elastic material within the front region and the back region.

17 Claims, 7 Drawing Sheets

(56) References Cited

U.S. PATENT DOCUMENTS

| | | | |
|---|---|---|---|
| 8,357,133 B2 | 1/2013 | Vasic et al. | |
| 8,529,536 B2 | 9/2013 | Tsang et al. | |
| 8,834,437 B2 | 9/2014 | Borrero et al. | |
| 9,265,669 B2 | 2/2016 | Bennett et al. | |
| 11,497,659 B2 | 11/2022 | You et al. | |
| 2002/0177829 A1 | 11/2002 | Fell et al. | |
| 2004/0010241 A1 | 1/2004 | Sanders et al. | |
| 2004/0225270 A1 | 11/2004 | Hermansson et al. | |
| 2010/0163161 A1* | 7/2010 | Gilgenbach | A61F 13/49017 156/155 |
| 2010/0168705 A1* | 7/2010 | Stabelfeldt | A61F 13/4902 604/385.29 |
| 2011/0112500 A1 | 5/2011 | Wenzel et al. | |
| 2011/0160692 A1* | 6/2011 | Wilkes | A61F 13/15756 156/267 |
| 2012/0253310 A1 | 10/2012 | Hahn et al. | |
| 2012/0283681 A1* | 11/2012 | Lohoff | D06C 15/08 604/385.01 |
| 2013/0152360 A1* | 6/2013 | Schoultz | A61F 13/15764 29/428 |
| 2013/0211366 A1 | 8/2013 | Gassner et al. | |
| 2015/0202094 A1* | 7/2015 | Inoue | A61F 13/4902 604/385.16 |
| 2016/0184145 A1 | 6/2016 | Morimoto | |
| 2018/0036183 A1 | 2/2018 | Espinosa de los Monteros et al. | |
| 2018/0042788 A1 | 2/2018 | Kurohara et al. | |
| 2018/0200121 A1* | 7/2018 | Eriksson | A61F 13/49017 |
| 2018/0333313 A1 | 11/2018 | LaVon et al. | |
| 2019/0374403 A1 | 12/2019 | Wang et al. | |

FOREIGN PATENT DOCUMENTS

| | | | |
|---|---|---|---|
| CN | 103826588 A | | 5/2014 |
| CN | 105073079 A | | 11/2015 |
| CN | 106999315 A | | 8/2017 |
| CN | 107106356 A | | 8/2017 |
| CN | 107582254 A | | 1/2018 |
| CN | 110022819 A | | 7/2019 |
| CN | 110337285 A | | 10/2019 |
| EP | 2483078 B1 | | 4/2017 |
| KR | 1020170127038 A | | 11/2017 |
| WO | 2017058069 A1 | | 4/2017 |
| WO | WO-2017105521 A1 | * | 6/2017 |

OTHER PUBLICATIONS

Co-pending U.S. Appl. No. 17/753,989, filed Mar. 21, 2022, by Borkovetz et al. for “Absorbent Article”.

Co-pending U.S. Appl. No. 17/753,990, filed Mar. 21, 2022, by Borkovetz et al. for “Absorbent Article”.

Co-pending U.S. Appl. No. 17/753,984, filed Mar. 21, 2022, by Borkovetz et al. for “Absorbent Article”.

* cited by examiner

ABSORBENT ARTICLE

BACKGROUND OF THE DISCLOSURE

Child care, feminine care, and adult hygiene-related absorbent personal care articles are often used to protect a wearer's outer garments from soiling, and to collect and retain body exudates such as menses, blood, feces, and urine. Such articles are often presented in disposable garment-like product formats (as opposed to inserts, pads, or liners) and are worn as undergarments in the place of traditional underwear. They are most commonly placed on a wearer by being pulled up about a wearer's legs towards the wearer's lower abdomen and placed adjacent a wearer's crotch region during use.

Today, many wearers of absorbent garment-like articles include adults who experience various forms of incontinence. Primary desired attributes of such garments include the garment retaining body exudate, minimal or no leakage of body exudate, close-to-body fit of the garment, and that it resembles traditional woven underwear. Consumers are interested in such attributes as there is a desire to enhance the overall personal experience of using such products while reducing incontinence-related stigma. Consumers want a garment that will meet their needs without signaling to others that they are wearing such absorbent garment-like articles. Absorbent article stigmas are aggravated by product designs which can feel bulky when in use, are ill-fitting and uncomfortable for the wearer to wear, do not fit close to the body and, therefore, may gap away from the wearer's body producing an outline that can be seen through a wearer's clothing, may be manufactured from materials that can create relatively high levels of noise during use due to the specific product construction materials, and by an overall artificial visual appearance of such products when viewed by the wearer and also by third parties.

In order to improve the fit of garment-like articles, many garment-like articles are formed by positioning an absorbent assembly between or otherwise bonded to at least one stretchable or elastomeric outer layer of the garment-like article. Garments with active elastic materials positioned over and around the absorbent material can result in the absorbent material bunching up. Such bunching of the absorbent material can create fit and discretion problems. From a fit standpoint, bunched up absorbent material is less likely to lie snugly against the body, potentially increasing the incidence of leakage. From a discretion standpoint, excessive bunching tends to make the product more bulky and therefore more visible under clothing. This circumstance is particularly problematic for incontinence articles, such as enuresis pants and adult pull-on style disposable absorbent underwear, as the wearers of such products generally are embarrassed about their condition and wish to employ protection which is as discreet as possible.

There is a need for an absorbent article having an improved fit about the lower torso of the wearer. There is a need for an absorbent article having elasticized waist regions that are less likely to cause undesirable gathering and bunching of the absorbent material.

SUMMARY OF THE DISCLOSURE

In various embodiments, an absorbent article can have a longitudinal direction and a transverse direction; a longitudinal axis and a transverse axis; a front region comprising a front waist edge, a first longitudinal direction side edge, a second longitudinal direction side edge transversely opposed to the first longitudinal direction side edge, a front region elastomeric panel comprising a first elastic material positioned between a first nonwoven material and a second nonwoven material; a back region comprising a back waist edge, a third longitudinal direction side edge, a fourth longitudinal direction side edge transversely opposed to the third longitudinal direction side edge, a back region elastomeric panel comprising a second elastic material positioned between a third nonwoven material and a fourth nonwoven material; a first side seam formed by bonding the first longitudinal direction side edge of the front region to the third longitudinal direction side edge of the back region and a second side seam formed by bonding the second longitudinal direction side edge of the front region to the fourth longitudinal direction side edge of the back region; a crotch region located between the front region and the back region and interconnecting the front region and the back region; an article length measured from the front waist edge to the back waist edge; and an absorbent core wherein a first portion of the absorbent core is located in the crotch region, a second portion of the absorbent core is located in a portion of the front region wherein the second portion of the absorbent core is in an overlapping configuration with a portion of the first elastic material and defining a front overlap region wherein the first elastic material located in the front overlap region is elastomeric in the transverse direction, and a third portion of the absorbent core is located in a portion of the back region wherein the third portion of the absorbent core is in an overlapping configuration with a portion of the second elastic material and defining a back overlap region wherein a first portion of the second elastic material located in the back overlap region is non-elastomeric in the transverse direction and defines a first non-elastomeric region having a first length dimension and a first width dimension and a second portion of the second elastic material located in the back overlap region is non-elastomeric in the transverse direction and defines a second non-elastomeric region having a second length dimension and a second width dimension wherein the second width dimension of the second non-elastomeric region is less than the first width dimension of the first non-elastomeric region.

In various embodiments, the first elastic material and the second elastic material is a plurality of elastomeric strands. In various embodiments, the first elastic material and the second elastic material is a polymeric film sheet.

In various embodiments, the absorbent article can have an absorbent article narrowest width in the transverse direction positioned in the crotch region and between the transverse axis and the front waist edge. In various embodiments, the absorbent article can have a front region width in the transverse direction from the first longitudinal direction side edge to the second longitudinal direction side edge wherein the absorbent article narrowest width is less than 25% of the front region width. In various embodiments, the absorbent article can have a first article sub-length measured from the front waist edge to the absorbent article narrowest width and a second article sub-length measured from the back waist edge to the absorbent article narrowest width wherein the first article sub-length is less than the second article sub-length. In various embodiments, the first article sub-length is less than 45% of the article length and the second article sub-length is greater than 55% of the article length.

In various embodiments, the absorbent core further comprises an absorbent core midpoint which is positioned between the absorbent article narrowest width and the transverse axis. In various embodiments, the absorbent core midpoint is offset in the longitudinal direction from the absorbent article narrowest width by a distance from 1% to 5% of the article length. In various embodiments, the absorbent article midpoint is offset in the longitudinal direction from the transverse axis by a distance from 6% to 15% of the article length.

In various embodiments, the back region further comprises a leg elastic.

In various embodiments, the absorbent article can have a first longitudinally extending elastic material located in the crotch region of the absorbent article and separated from the absorbent core in the transverse direction at the location of each of the absorbent article narrowest width and the transverse axis by a spatial distance of at least 1.5% of the front region width. In various embodiments, the absorbent article can have a second longitudinally extending elastic material located in the crotch region of the absorbent article and separated from the absorbent core in the transverse direction at the location of each of the absorbent article narrowest width and the transverse axis by a spatial distance of at least 1.5% of the front region width.

In various embodiments, the first non-elastomeric region is positioned closer to the back waist edge than the second non-elastomeric region. In various embodiments, the first non-elastomeric region is adjacent to the second non-elastomeric region. In various embodiments, the second non-elastomeric region is symmetrically positioned along the transverse direction of the back overlap region.

Figure 1:
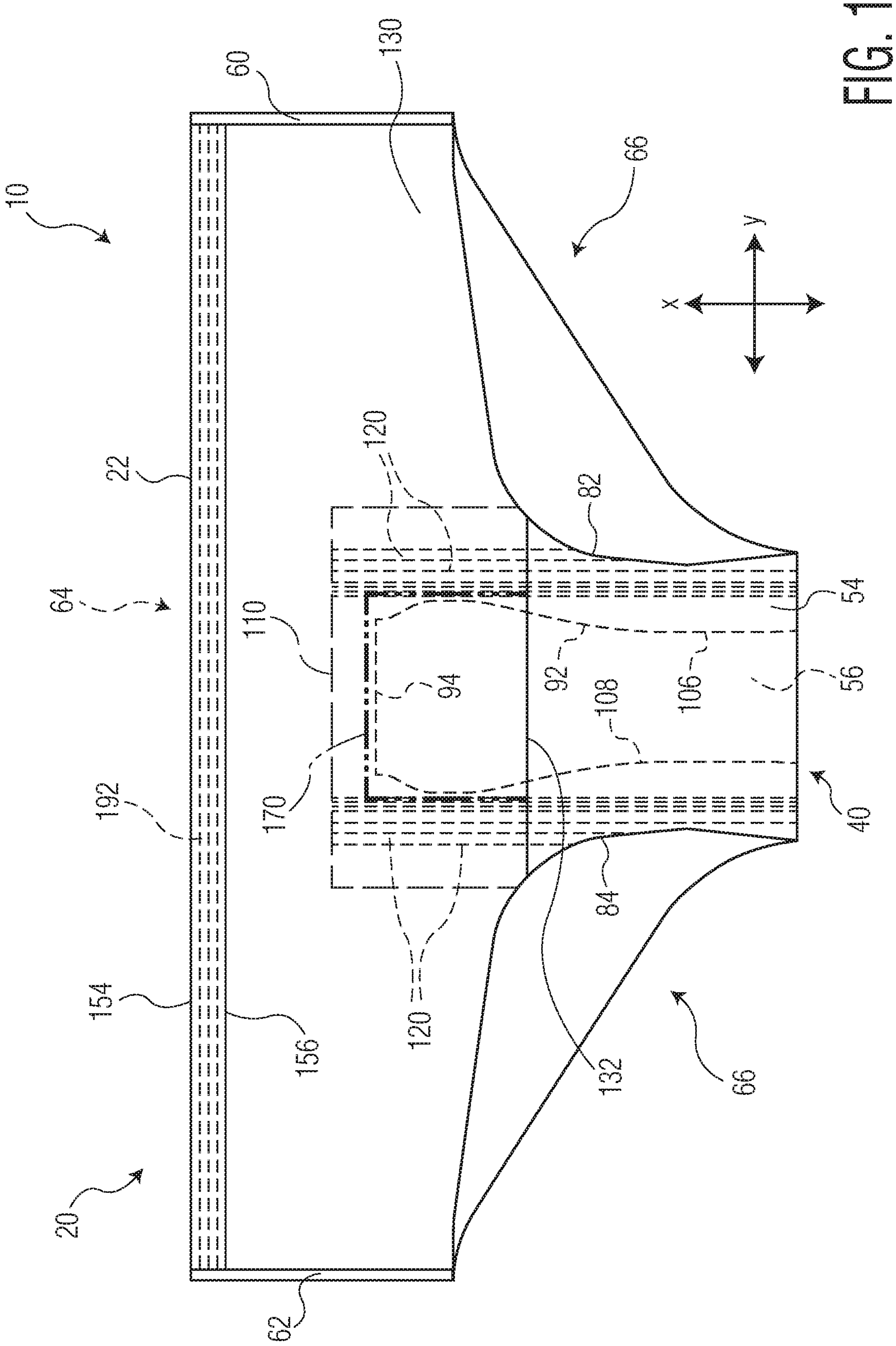
FIG. 1 is an illustration of a front view of an embodiment of an absorbent article in a pull-on, pant-like configuration.

Repeat use of reference characters in the present specification and drawings is intended to represent the same or analogous features or elements of the disclosure.

DETAILED DESCRIPTION OF THE DISCLOSURE

The present disclosure is directed towards an absorbent article such as a garment-like absorbent article. The absorbent article has a front region, a back region, and a crotch region extending between and interconnecting the front region and the back region. Each of the front region and the back region can have an elastic material. The absorbent article can have an absorbent core wherein a portion of the absorbent core can be located in the crotch region, a portion of the absorbent core can be located in a portion of the front region, and a portion of the absorbent core can be located in a portion of the back region. Within each of the front region and the back region, an overlapping region can exist where the absorbent core is in an overlapping configuration with the elastic material within the front region and the back region.

As used herein, the term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, enuresis garments, menstrual pants, and adult incontinence garments, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Figure 2:
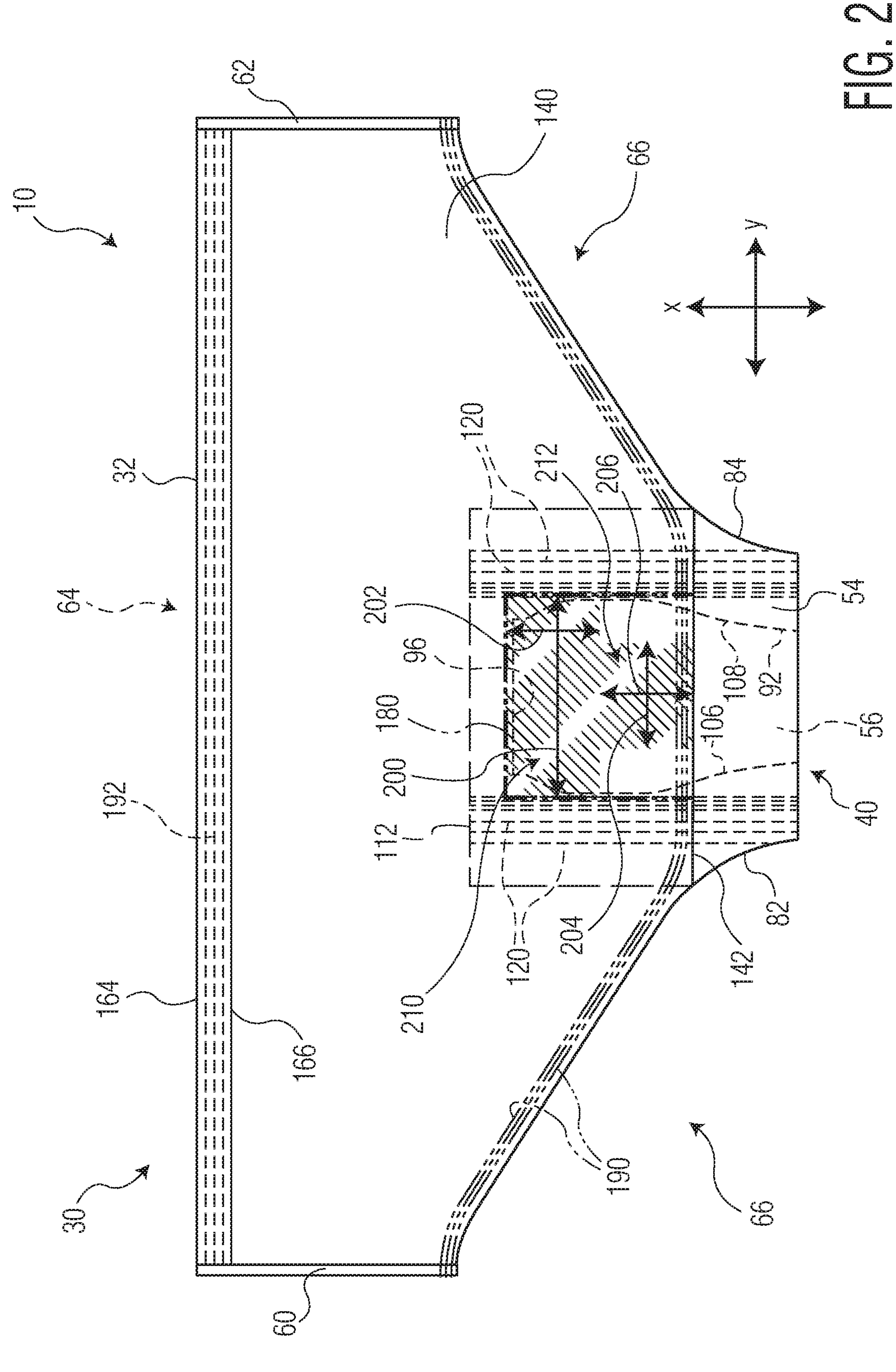
FIG. 2 is an illustration of a back view of the absorbent article of FIG. 1.
Figure 3:
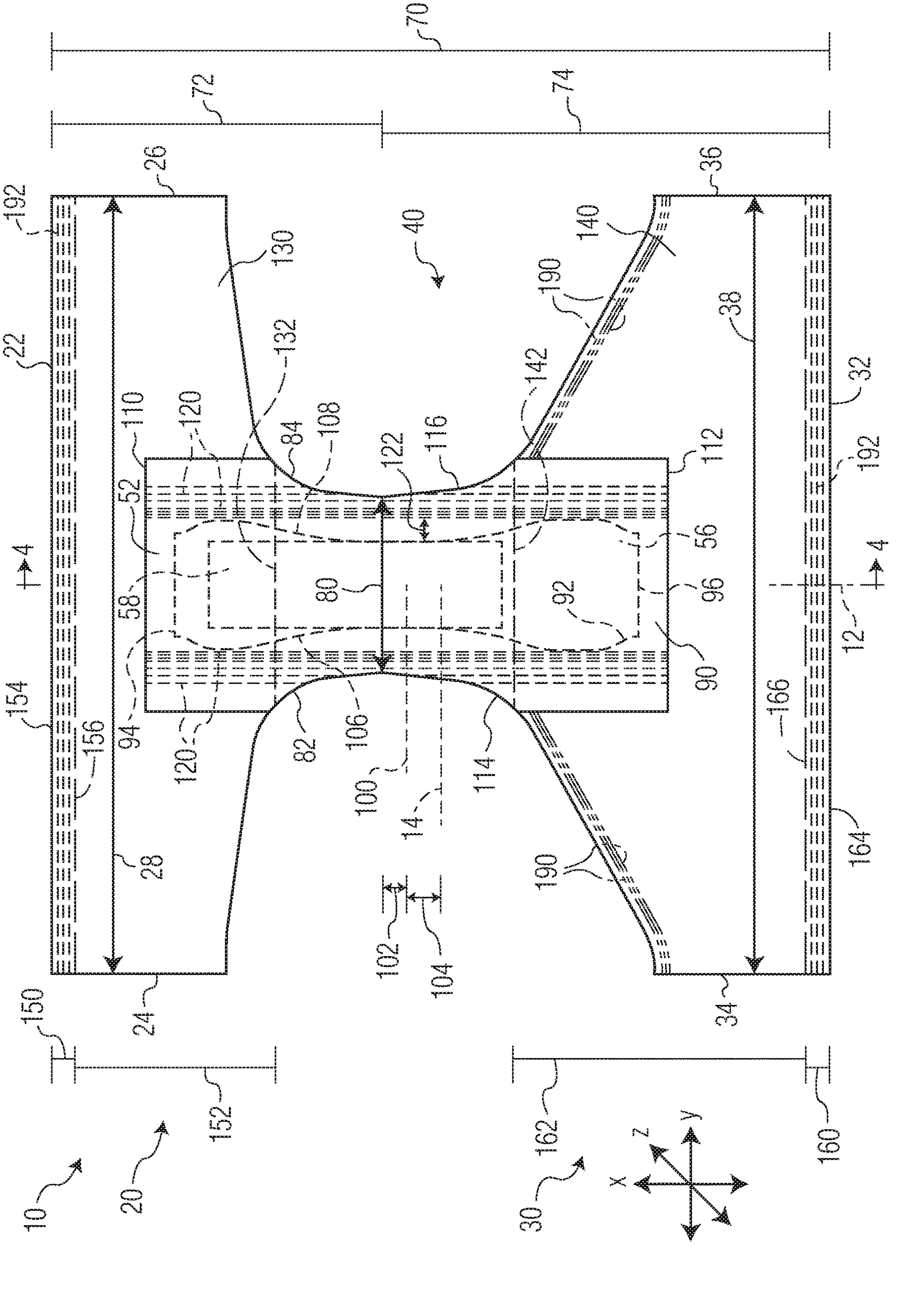
FIG. 3 is an illustration of a plan view of an embodiment of the absorbent article of FIG. 1 in a longitudinally and transversely stretched and laid-flat configuration prior to the joining of the front and back regions with the surface of the absorbent article that faces the wearer when the absorbent article is worn facing the viewer.
Figure 4:
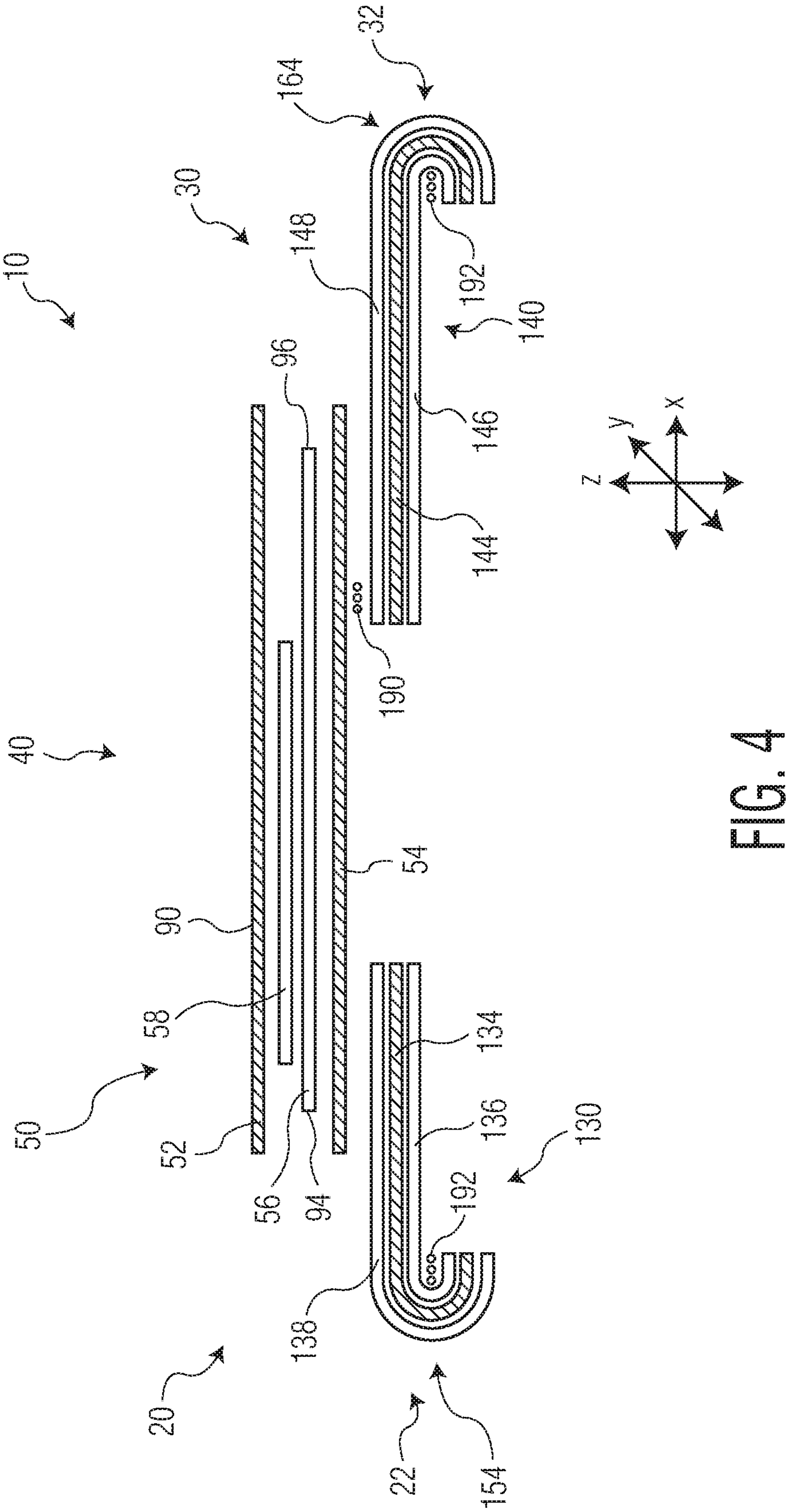
FIG. 4 is an illustration of a cross-sectional view of an embodiment of the absorbent article of FIG. 3 taken along line 4-4.

Referring to FIGS. 1-4, an illustration of an exemplary embodiment of an absorbent article 10 is illustrated. FIG. 1 provides an illustration of an embodiment of a front view of the absorbent article 10 in a pull-on, pant-like configuration, FIG. 2 provides an illustration of a back view of the absorbent article 10 of FIG. 1 in a pull-on, pant-like configuration, FIG. 3 provides an illustration of a plan view of an embodiment of the absorbent article 10 of FIG. 1 in a longitudinally and transversely stretched and laid-flat configuration prior to the joining of the front and back regions, 20 and 30, with the surface of the absorbent article 10 that faces the wearer when the absorbent article 10 is worn facing the viewer, and FIG. 4 provides an illustration of a cross-sectional view of an embodiment of the absorbent article 10 of FIG. 3 taken along line 4-4. Although for illustrative purposes certain features of the present disclosure can be described and illustrated with respect to an adult incontinence garment, the various aspects and embodiments of the present disclosure are also suitable for use with diapers, youth pants, swim pants, training pants, enuresis garments, menstrual pants, and the like.

The absorbent article 10 has a longitudinal direction (X), a transverse direction (Y), and a depth direction (Z). The absorbent article 10 can have a longitudinal axis 12 and a transverse axis 14. The absorbent article 10 is intended to be worn about the lower torso of a human and can have a front region 20, a back region 30, and a crotch region 40 extending between and interconnecting the front region 20 and the back region 30. The front region 20 and the back region 30 are those regions of the absorbent article 10 that are fitted circumferentially around at least the lower torso of the wearer of the absorbent article 10 including, for example, the wearer's abdomen, lower back, buttock, and hips. The front region 20 will be positioned on the anterior region of the wearer's lower torso while the back region will be positioned on the posterior region of the wearer's lower torso. The crotch region 40 of the absorbent article 10 is that region of the absorbent article 10 that will be positioned between the wearer's legs when the absorbent article 10 is fitted onto the wearer.

The front region 20 has a front waist edge 22, a first longitudinal direction front side edge 24, and a second longitudinal direction front side edge 26 transversely opposed to the first longitudinal direction front side edge 24. The back region 30 has a back waist edge 32, a first longitudinal direction back side edge 34, and a second longitudinal direction back side edge 36 transversely opposed to the first longitudinal direction back side edge 34. To place the absorbent article 10 into a suitable configuration for wearing about the lower torso of the wearer, the first longitudinal direction front side edge 24 can be bonded to the first longitudinal direction back side edge 34 to form a first side seam 60 and the second longitudinal direction front side edge 26 can be bonded to the second longitudinal direction back side edge 36 to form a second side seam 62. Forming the side seams, 60 and 62, can create a wearable absorbent article 10 having a waist opening 64 and a pair of leg openings 66.

The front region 20 can have a front region width 28 measured in the transverse direction (Y) between the first longitudinal direction front side edge 24 and the second longitudinal direction front side edge 26. The front region width 28 is measured with the absorbent article 10 fully extended in the transverse direction (Y) such as illustrated in FIG. 3 when the absorbent article 10 is in a longitudinally and transversely stretched and laid-flat configuration prior to the joining of the front and back regions to form the side seams, 60 and 62. As used herein, the term "fully extended" describes the condition wherein the absorbent article 10 is extended in a given direction to the point where any further extension in said direction would result in one or more material failures (e.g., rupture or permanent deformation). In embodiments wherein the first longitudinal direction front side edge 24 and the second longitudinal direction front side edge 26 are not parallel with the longitudinal direction (X) (not illustrated), the front region width 28 is the maximum width measured parallel with the transverse direction (Y) from any point on the first longitudinal direction front side edge 24 to any point on the second longitudinal direction front side edge 26. In various embodiments, the front region width 28 may be from 600 or 625 mm to 850 or 900 mm.

The back region 30 can have a back region width 38 measured in the transverse direction (Y) between the first back side edge 34 and the second back side edge 36. The back region width 38 is measured with the absorbent article 10 fully extended in the transverse direction (Y) such as illustrated in FIG. 3 when the absorbent article 10 is in a longitudinally and transversely stretched and laid-flat configuration prior to the joining of the front and back regions to form the side seams, 60 and 62. In embodiments wherein the first back side edge 34 and the second back side edge 36 are not parallel with the longitudinal direction (X) (not illustrated), the back region width 38 is the maximum width measured parallel with the transverse direction (Y) from any point on the first back side edge 34 to any point on the second back side edge 36. In various embodiments, the back region width 38 may be from 600 or 625 mm to 850 or 900 mm.

The absorbent article 10 has an article length 70 as measured in the longitudinal direction (X) from the front waist edge 22 to the back waist edge 32 as illustrated in FIG. 3. The article length 70 is measured with the absorbent article 10 fully extended in the longitudinal direction (X) such as illustrated in FIG. 3 when the absorbent article 10 is in a longitudinally and transversely stretched and laid-flat configuration prior to the joining of the front and back regions to form the side seams, 60 and 62. In various embodiments, the article length 70 may be at least 600, 620, 640, 660, 680, 700, 720, 740, 760, 780, 800, or 820 mm.

The crotch region 40 is disposed in the longitudinal direction (X) between and interconnecting the front region 20 and the back region 30. The absorbent article has an absorbent article narrowest width 80 located within the crotch region 40 of the absorbent article 10. The absorbent article narrowest width 80 is measured in the transverse direction (Y) as the narrowest dimension between a first leg edge 82 and a second leg edge 84 such as illustrated in FIG. 3. The absorbent article narrowest width 80 is measured with the absorbent article 10 in a longitudinally and transversely stretched and laid-flat configuration prior to the joining of the front and back regions to form the side seams, 60 and 62. In various embodiments, the absorbent article narrowest width 80 is less than 25% or 20% of the front region width 28. For example, in various embodiments, the absorbent article narrowest width 80 may be about 150 mm and the front region width 28 may be about 630 mm or 740 mm. In such embodiments, the absorbent article narrowest width 80 may be about 24% or 20% of the front region width 28, respectively. As another example, in various embodiments, the absorbent article narrowest width 80 may be about 150 mm and the front region width 80 may be about 750 mm or 880 mm. In such embodiments, the absorbent article narrowest width 80 may be about 20% or 17% of the front region width 28, respectively. The lower the percentage of the absorbent article narrowest width 80, relative to the front region width 28, the more shaped the absorbent article 10 is within the crotch region 40. In other words, the higher the percentage (up to 100%) the more rectangular the absorbent article 10 is within the crotch region 40. An absorbent article 10 having a more rectangular shape within the crotch region 40 may provide too much bulk of an absorbent article 10 between the wearer's legs which fails to follow the contours of the wearer's legs. This can result in the absorbent article 10 bunching up between the wearer's legs, protruding away from the body of the wearer, and not fitting close to the body of the wearer at the location where body exudate exits the body of the wearer. Providing a non-rectangular shape to the absorbent article 10 within the crotch region 40 of the absorbent article 10 can remove bulk from between the wearer's legs and allow the absorbent article 10 to better fit against and between the contours of the wearer's legs. This can allow for improved conformance of the absorbent article 10 to the body of the wearer.

In various embodiments, the absorbent article narrowest width 80 is positioned between the front waist edge 22 and the transverse axis 14 of the absorbent article 10. In such embodiments, the absorbent article narrowest width 80 is not in an overlapping alignment with the transverse axis 14 of the absorbent article 10. The absorbent article narrowest width 80 can apportion the article length 70 into a first article sub-length 72 and a second article sub-length 74. The first article sub-length 72 can be measured in the longitudinal direction (X) from the front waist edge 22 to the absorbent article narrowest width 80 when the absorbent article 10 is in a longitudinally and transversely stretched and laid-flat configuration prior to the joining of the front and back regions to form the side seams, 60 and 62. The second article sub-length 74 can be measured in the longitudinal direction (X) from the back waist edge 32 to the absorbent article narrowest width 80 when the absorbent article 10 is in a longitudinally and transversely stretched and laid-flat configuration prior to the joining of the front and back regions to form the side seams, 60 and 62. In various embodiments, the first article sub-length 72 is less than the second article sub-length 74. In various embodiments, the first article sub-length 72 can be less than 45% or 40% of the total article length 70. In various embodiments, the second article sub-length 74 can be greater than 55% or 60% of the total article length 70. Wearers of absorbent articles 10 have body shapes in a variety of shapes, sizes, and curvature, and are generally not symmetrical. Placing a symmetrical about the transverse axis 14 absorbent article 10 on a body which is not symmetrical can result in a reduction in proper fit of the absorbent article 10 on the body of the wearer. Positioning the absorbent article narrowest width 80 closer to the front waist edge 22, and not in alignment with the transverse axis 14, can provide for a non-symmetrical about the transverse axis 14 absorbent article 10. As a result, when the absorbent article narrowest width 80 is positioned between the legs of the wearer a greater proportion of the absorbent article 10 is positioned on the posterior side of the wearer's body providing for better coverage of the buttocks of the wearer of the absorbent article 10.

The absorbent article 10 can also include an absorbent assembly 50. The absorbent assembly 50 can extend in the longitudinal direction (X) of the absorbent article 10 from the front region 20, through the crotch region 40, and to the back region 30. In various embodiments, the absorbent assembly 50 can have at least a topsheet layer 52, a backsheet layer 54, and an absorbent core 56 positioned between the topsheet layer 52 and the backsheet layer 54. In various embodiments, the absorbent assembly 50 can have at least a topsheet layer 52, a backsheet layer 54, an absorbent core 56 positioned between the topsheet layer 52 and the backsheet layer 54, and a surge layer 58 positioned between the absorbent core 56 and the topsheet layer 52. The topsheet layer 52 can be bonded to the backsheet layer 54 beyond the outermost edge of the absorbent core 56 to form a perimeter seal for the absorbent assembly 50. The perimeter seal can contain the body exudates within the absorbent assembly 50 of the absorbent article 10.

The topsheet layer 52 defines a body facing surface 90 of the absorbent assembly 50 that may directly contact the body of the wearer and is liquid permeable to receive body exudates. The topsheet layer 52 is desirably provided for comfort and functions to direct body exudates away from the body of the wearer, through its own structure, and towards the absorbent core 56. The topsheet layer 52 desirably retains little to no liquid in its structure, so that it provides a relatively comfortable and non-irritating surface next to the skin of the wearer of the absorbent article 10.

The topsheet layer 52 can be a single layer of material, or alternatively, can be multiple layers that have been laminated together. The topsheet layer 52 can be constructed of any material such as one or more woven sheets, one or more fibrous nonwoven sheets, one or more aperture film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 52.

In various embodiments the topsheet layer 52 can be constructed from various nonwoven webs such as meltblown webs, spunbond webs, hydroentangled spunlace webs, or through air bonded carded webs. Examples of suitable topsheet layer 52 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 52 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 52, each of which is hereby incorporated by reference thereto in its entirety. Additional topsheet layer 52 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 52 may contain a plurality of apertures formed therethrough to permit body exudates to pass more readily into the absorbent core 56. The apertures may be randomly or uniformly arranged throughout the topsheet layer 52. The size, shape, diameter, and number of apertures may be varied to suit an absorbent article's 10 particular needs.

In various embodiments, the topsheet layer 52 can have a basis weight ranging from about 5, 10, 15, 20, or 25 gsm to about 50, 100, 120, 125, or 150 gsm. For example, in an embodiment, a topsheet layer 52 can be constructed from a through air bonded carded web having a basis weight ranging from about 15 gsm to about 100 gsm. In another example, a topsheet layer 52 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 52 can be at least partially hydrophilic. In various embodiments, a portion of the topsheet layer 52 can be hydrophilic and a portion of the topsheet layer 52 can be hydrophobic. In various embodiments, the portions of the topsheet layer 52 which can be hydrophobic can be either an inherently hydrophobic material or can be a material treated with a hydrophobic coating.

In various embodiments, the topsheet layer 52 can be a multicomponent topsheet layer 52 such as by having two or more different nonwoven or film materials, with the different materials placed in separate locations in the transverse direction (Y) of the absorbent assembly 50. For example, the topsheet layer 52 can be a two layer or multicomponent material having a central portion positioned along and straddling a longitudinal axis 12 of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating.

Examples of constructions of multi-component topsheet layers are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 52 can be positioned symmetrically about the absorbent article 10 longitudinal axis 12. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 52. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 52. The selection of such topsheet layer 52 materials can vary based upon the overall desired attributes of the topsheet layer 52. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 52 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent assembly 50 side edges when viewed from above the topsheet layer 52. The film layer may also serve as a barrier layer to prevent rewet of the topsheet layer 52 as well as to prevent the flow of fluid off the side edges of the absorbent assembly 50. In various embodiments, the side portions can be laminates such as a spunbond-meltblown-meltblown-spunbond layer ("SMMS") laminate, spunbond-film laminate, or alternatively, other nonwoven laminate combinations.

The backsheet layer 54 of the absorbent assembly 50 is generally liquid impermeable and is the portion of the absorbent assembly 50 which faces the garments of the wearer. The backsheet layer 54 can permit the passage of air or vapor out of the absorbent article 10 while still blocking the passage of liquids. Any liquid impermeable material may generally be utilized to form the backsheet layer 54. The backsheet layer 54 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the backsheet layer 54 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a backsheet layer 54 can be a polyethylene film such as that obtainable from Pliant Corp., Schaumburg, IL, USA. Another example can include calcium carbonate-filled polypropylene film. In still another embodiment, the backsheet layer 54 can be a hydrophobic nonwoven material with water barrier properties such as a nonwoven laminate, an example of which can be a spunbond, meltblown, meltblown, spunbons, four-layered laminate.

In various embodiments, the backsheet layer 54 can be a two layer construction, including an outer layer material and an inner layer material which can be bonded together. The outer layer can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer can be a 20 gsm spunbond polypropylene non-woven web. The inner layer can be either vapor permeable (i.e., "breathable") or vapor impermeable. The inner layer may be manufactured from a thin plastic film, although other liquid impermeable materials may also be used. The inner layer can inhibit liquid body exudates from leaking out of the absorbent assembly 50 and wetting articles, such as bed sheets and clothing, as well as the wearer and caregiver. An example of a material for an inner layer can be a printed 19 gsm Berry Plastics XP-8695H film or equivalent commercially available from Berry Plastics Corporation, Evansville, IN, U.S.A.

The backsheet layer 54 can, therefore, be of a single or multiple layer construction, such as of multiple film layers or laminates of film and nonwoven fibrous layers. Suitable backsheet layers 206 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

An absorbent core 56 can be positioned between the topsheet layer 52 and the backsheet layer 54 of the absorbent article 10. In various embodiments, the absorbent core 56 can extend in the longitudinal direction (X) of the absorbent assembly 50. The absorbent core 56 can have a first portion located in the crotch region 40 of the absorbent article 10. In various embodiments, the absorbent core 56 can have a second portion located in a portion of at least one of the front region 20 or the back region 30. In various embodiments, the absorbent core 56 can have a first portion located within the crotch region 40 and a second portion located in a portion of the front region 20. In various embodiments, the absorbent core 56 can have a first portion located within the crotch region 40 and a second portion located in a portion of the back region 30. In various embodiments, an absorbent core 56 can have a first portion located within the crotch region 40, a second portion located in a portion of the front region 20, and a third portion located in a portion of the back region 30.

The absorbent core 56 can generally be any single layer structure or combination of layer components, which can demonstrate some level of compressibility, conformability, be non-irritating to the wearer's skin, and capable of absorbing and retaining liquids and other body exudates. In various embodiments, the absorbent core 56 can be formed from a variety of different materials and can contain any number of desired layers. For example, the absorbent core 56 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of wood pulp fluff can be identified with the trade designation NB416, available from Weyerhaeuser Corp., and is a bleached, highly absorbent wood pulp containing primarily soft wood fibers.

In various embodiments, if desired, the absorbent core 56 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 56 in any amount as desired.

Regardless of the combination of absorbent materials used in the absorbent core 56, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The absorbent core 56 can have a perimeter edge 92 formed by a first transverse direction end edge 94, a second transverse direction end edge 96 opposed to the first transverse direction end edge 94, and a pair of opposing longitudinal direction side edges, 106 and 108, extending between and connecting the first transverse direction end edge 94 and the second transverse direction end edge 96. The perimeter edge 92 defines the overall shape of the absorbent core 56. In various embodiments, the perimeter edge 92 defines a shape of an absorbent core 56 which is any shape as deemed suitable for the absorbent article 10.

The absorbent core 56 can have an absorbent core midpoint 100 which is the location halfway between the first transverse direction end edge 94 of the absorbent core 56 and the second transverse direction end edge 96 of the absorbent core 56. The absorbent core midpoint 100 is positioned within the crotch region 40 of the absorbent article 10 and between the absorbent article narrowest width 80 and the transverse axis 14 of the absorbent article 10. The absorbent core midpoint 100, therefore, does not coincide with either the absorbent article narrowest width 80 or the transverse axis 14 of the absorbent article 10. In various embodiments, the absorbent core midpoint 100 is offset from the absorbent article narrowest width 80 by a distance 102 in the longitudinal direction (X) of at least 10, 12, 14, 16, 18, 20, 22, 24, 26, 28, or 30 mm. In various embodiments, the absorbent core midpoint 100 is offset from the absorbent article narrowest width 80 by a distance 102 in the longitudinal direction (X) from about 10, 12, 14, 16, or 18 mm, to about 20, 22, 24, 26, 28, or 30 mm. In various embodiments, the absorbent core midpoint 100 is offset from the absorbent article narrowest width 80 by a distance 102 in the longitudinal direction (X) of at least 1% of the absorbent article 10 total article length 70. In various embodiments, the absorbent core midpoint 100 is offset from the absorbent article narrowest width 80 by a distance 102 in the longitudinal direction (X) from about 1 or 2% to about 4 or 5% of the absorbent article 10 total article length 70. In various embodiments, the absorbent core midpoint 100 is offset from the transverse axis 14 of the absorbent article 10 by a distance 104 in the longitudinal direction (X) of at least 50, 52, 54, 56, 58, 60, 62, 64, 66, 68, 70, 72, 74, or 76 mm. In various embodiments, the absorbent core midpoint 100 is offset from the transverse axis 14 of the absorbent article 10 by a distance 104 in the longitudinal direction (X) from about 50, 52, 54, 56, 58, 60, or 62 mm to about 64, 66, 68, 70, 72, 74, or 76 mm. In various embodiments, the absorbent core midpoint 100 is offset from the transverse axis 14 of the absorbent article 10 by a distance 104 in the longitudinal direction (X) of from about 6 or 8% to about 9 or 15% of the absorbent article 10 total article length 70. As described herein, an absorbent article 10 having a more rectangular shape within the crotch region 40 may provide too much absorbent article bulk between the legs of the wearer of the absorbent article 10 which can result in the absorbent article bunching up between the wearer's legs, protruding away from the body of the wearer and not fitting close to the body of the wearer. Additionally, wearers of absorbent articles have body shapes which are a variety of shapes, sizes, and curvature, and generally not symmetrical. Positioning, the absorbent article narrowest width 80 closer to the front waist edge 22 can provide for a non-symmetrical absorbent article 10 wherein a greater proportion of the absorbent article 10 is positioned on the posterior side of the wearer's body providing for better coverage of the buttocks of the wearer of the absorbent article 10 and a lesser proportion of the absorbent article 10 is positioned on the anterior side of the wearer's body providing for a reduction of friction between the material of the absorbent article 10 and the wearer's legs when they move. Positioning the absorbent core midpoint 100 between the absorbent article narrowest width 80 and the transverse axis 14 can place the absorbent core 56 where it is needed most for capture of body exudate released from the wearer of the absorbent article 10 and minimize the bulkiness of the material of the absorbent core 56 between the legs of the wearer of the absorbent article 10.

By way of example, suitable materials and/or structures for the absorbent core 56 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al. each of which is hereby incorporated by reference thereto in its entirety.

In various embodiments, an absorbent core 56 can be a single layer structure and can include, for example, a matrix of cellulosic fluff and superabsorbent material. In various embodiments, an absorbent core 56 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 56 may be constructed of an airlaid material and the garment facing layer of the absorbent core 56 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

In various embodiments, the absorbent assembly 50 can include a surge layer 58 positioned between the absorbent core 56 and the topsheet layer 52. The surge layer 58 can be adapted to work with the absorbent core 56 in absorbing body exudates. In various embodiments, the surge layer 58 can have a higher void volume than the absorbent core 56 to quickly intake and hold body exudates so that the absorbent core 56 has time to absorb the body exudates without such body exudates leaking from the absorbent article 10. The surge layer 58 can take on any size and shape as desired and as deemed suitable. For example, in FIG. 3, the surge layer 58 is illustrated in the shape of a rectangle and has a size dimension smaller than the absorbent core 56.

The absorbent assembly 50 can have a first transverse direction end edge 110, a second transverse direction end edge 112 opposed to the first transverse direction end edge 110, and a pair of opposing longitudinal direction side edges, 114 and 116, extending between and connecting the first transverse direction end edge 110 and the second transverse direction end edge 112. In various embodiments, such as illustrated in FIGS. 1-3, the non-linear portions of the longitudinal direction side edges, 114 and 116, of the absorbent assembly 50 can be arcuate and can form portions of the first leg side edge 82 and the second leg side edge 84, respectively, of the absorbent article 10.

The absorbent article 10 can have longitudinally extending elastic material 120 wherein a portion of the elastic material 120 is located at least within the crotch region 40 of the absorbent article 10 and positioned between each of the first longitudinal direction side edge 106 of the absorbent core 56 and the first leg side edge 82 of the absorbent article 10 and the second longitudinal direction side edge 108 of the absorbent core 56 and the second leg side edge 84 of the absorbent article 10. Each elastic material 120 can be an elastic strand, ribbon, or strip of elastic material. For example, with reference to FIG. 3, the elastic material 120 is a plurality of elastic strands extending longitudinally between the first longitudinal direction side edge 106 of the absorbent core 56 and the first leg side edge 82 of the absorbent article 10 and a plurality of elastic strands forming the elastic material 120 extending longitudinally between the second longitudinal direction side edge 108 of the absorbent core 56 and the second leg side edge 84 of the absorbent article 10. While the elastic material 120 is illustrated as longitudinally extending from the front region 20, through the crotch region 40, and to the back region 30, it is to be understood that the elastic material 120 can be positioned in only the crotch region 40, in a combination of the crotch region 40 and front region 20, in a combination of the crotch region 40 and back region 30, or in a combination, such as illustrated, of the crotch region 40, front region 20, and back region 30.

Each of the longitudinally extending elastic materials 120 can have an interior perimeter which is the portion of the elastic materials 120 closest to the absorbent core 56 without coming into a configuration such that it will overlay the absorbent core 56. The interior perimeter of each of the longitudinally extending elastic materials 120 can be positioned at a spatial distance 122 from the longitudinal direction side edges, 106 and 108, of the absorbent core 56. The spatial distance 122 of each of the longitudinally extending elastic materials 120 from each of the longitudinal direction side edges, 106 and 108, at the locations of each of the absorbent article narrowest width 80 and the transverse axis 14 can be a minimum of 15 mm. In various embodiments, the spatial distance 122 at each of the locations of the absorbent article narrowest width 80 and the transverse axis 14 can be from about 15, 17, 19, or 21 mm to about 23, 25, 27, 29, or 31 mm. In various embodiments, the spatial distance 122 at each of the locations of the absorbent article narrowest width 80 and the transverse axis 14 can be a minimum of 1.5, 2, 2.5, 3, 3.5, 4, 4.5, 5, or 5.5% of the front region width 28. In various embodiments, the spatial distance 122 can be uniform. In various embodiments, the spatial distance 122 can be non-uniform. Such a spatial distance 122 can allow for movement of the absorbent core 56 as the wearer moves their body. The spatial distance 122 can isolate the absorbent core 56 of the absorbent article 10 such that when the wearer of the absorbent article 10 moves their body and/or legs, the absorbent core 56 is not impacted by such movement of the wearer. If the longitudinally extending elastic materials 120 were not separated by a minimum spatial distance 122 from the absorbent core 56, the movement of the wearer could cause the elastic materials 120 to pull and twist the absorbent core 56 which can lead to movement of the absorbent core 56 out of proper placement for capturing body exudates. In various embodiments, the longitudinally extending elastic materials 120 can be non-linear or linear as they extend in the longitudinal direction (X) of the absorbent article 10.

As illustrated in FIGS. 1-4, the front region 20 of the absorbent article 10 can be constructed of an elastomeric panel 130. The elastomeric panel 130 of the front region 20 can be bordered by a front lower edge 132, the first front side edge 24, the second front side edge 26, and the front waist edge 22. The back region 30 can be constructed of an elastomeric panel 140. The elastomeric panel 140 of the back region 30 can be bordered by a back lower edge 142, the first back side edge 34, the second back side edge 36, and the back waist edge 32. The elastomeric panels, 130 and 140, can have elastic material, 134 and 144, respectively, such that the elastomeric panels, 130 and/or 140, upon application of a stretching force, are stretchable in the transverse direction (Y), and which upon release of the stretching force, contracts/returns at least a portion of its stretched length, desirably to its original dimension.

In various embodiments, the elastic material, 134 and 144, in each of the elastomeric panels, 130 and 140, can be elastomeric strands of material such as can be preformed from LYCRA brand fibers/yarns for example. LYCRA is a registered trademark of E.I. DuPont DeNemours Co., Wilmington, DE, U.S.A. The elastomeric strands can have a round, semi-circular, square, rectangular, oval, or other geometrical configuration. In various embodiments, the plurality of elastomeric strands can be elastomeric in at least the transverse direction of the absorbent article 10 and can extend from the first side edge, 24 or 34, to the second side edge, 26 or 36, of the elastomeric panels, 130 or 140, respectively. When present, the elastomeric strands can be positioned in a longitudinal direction spaced apart configuration. In various embodiments, the elastic material, 134 and 144, can be an elastomeric polymeric film layer. The elastomeric polymeric film layer can be elastomeric in at least the transverse direction of the absorbent article 10 and can extend from the first side edge, 24 or 34, to the second side edge, 26 or 36, of the elastomeric panels, 130 or 140, respectively. In various embodiments, a suitable elastomeric polymeric film layer can be a stretch-bonded laminate (SBL) in which an elastic core or middle layer is elongated before two opposing outer nonwoven web layers are bonded thereto. Another suitable material for the elastomeric polymeric film layer is a necked bonded laminate (NBL). The NBL material is a three layer laminate but the elastic core or middle layer is not pre-stretched prior to being attached to the two outer nonwoven web layers. Instead, the opposing outer nonwoven web layers are necked stretched before the elastic core or middle layer is bonded to them. Other examples of such elastomeric materials that can be used as an elastomeric polymeric film layer include a continuous filament stretch bonded laminate (CFSBL), a vertical filament laminate (VFL), a necked stretch bonded laminate (NSBL), or a necked thermal laminate (NTL). Combinations of such materials can also be used. Such materials are described in U.S. Pat. No. 4,720,415 to Vander Wielen et al., U.S. Pat. No. 5,366,793 to Fitts, et al., U.S. Pat. No. 5,385,775, to Wright, U.S. Pat. No. 6,969,441 to Welch et al., U.S. Pat. No. 6,978,486 to Zhou et al., U.S. Pat. No. 7,803,244 to Siqueira et al., and U.S. Pat. No. 5,226,992 to Morman et al., each of which are hereby incorporated by reference thereto in its entirety. The elastomeric laminates just described will typically include an elastomeric layer and at least one surface-bonded nonwoven web layer such as a meltblown, spunbond, or through-air bonded web.

To form each of the elastomeric panels, 130 and 140, the elastic material, 134 and 144, within the elastomeric panels, 130 and 140, can be sandwiched between a single nonwoven material which has been folded over onto itself or can be sandwiched between two separate nonwoven materials. For example, as illustrated in FIGS. 3 and 4, each of the elastomeric panels, 130 and 140, are formed by sandwiching an elastic material, 134 and 144, such as, for example, a polymeric film sheet, between a pair of nonwoven materials, 136 and 138, in the front region 20 and a pair of nonwoven materials, 146 and 148, in the back region 30. The elastic materials, 134 and 144, can be sandwiched and held between the nonwoven layers, 136, 138, 146, and 148, with adhesive, ultrasonic bonding, heat pressure sealing, or any other means deemed suitable.

Each of the elastomeric panels, 130 and 140, can have a first portion, 150 and 160, respectively, which can be the waist portion of the absorbent article 10. In various embodiments, each first portion, 150 and 160, of the elastomeric panels, 130 and 140, respectively, can have a length in the longitudinal direction (X) which is less than about 5, 4, or 3% of the absorbent article length 70. In the illustrative and exemplary embodiments of FIGS. 1-4, the first portion, 150 and 160, can be further illustrated as having a waist edge, 22 and 32, formed by folding a portion of the elastomeric panels, 130 and 140, onto itself creating a fold, 154 and 164, and placing a material edge, 156 and 166, on the exterior of the absorbent article 10. In various embodiments, the elastic material, 134 and 144, in each of the first portions, 150 and 160, of the elastomeric panels, 130 and 140, can have a uniform tension in the transverse direction (Y) and in the longitudinal direction (X). To create additional tension in the first portions, 150 and 160, of the elastomeric panels, 130 and 140, it may desirable to include secondary elastic material, such as, for example, elastic strands 192, within the fold, 154 and 164.

Each of the elastomeric panels, 130 and 140, can have a second portion, 152 and 162, respectively, which can be the chassis portion of the absorbent article 10. The second portion, 152 and 162, of each of the elastomeric panels, 130 and 140, respectively, can exclude the first portions, 150 and 160, and can extend in the longitudinal direction (X) from the first portions, 150 and 160, towards the crotch region 40 of the absorbent article 10. As described herein, in various embodiments, the absorbent core 56 can have a first portion in the crotch region 40 of the absorbent article 10 and a second portion located in a portion of at least one of the front region 20 and/or the back region 30. In such embodiments, the second portion of the absorbent core 56 located in a portion of at least one of the front region 20 and/or the back region 30 can be in an overlapping configuration with a portion of the elastic material, 134 and/or 144, in the respective second portions, 152 and/or 162, of the front region 20 and/or the back region 30. In various embodiments, the absorbent core 56 can have a first portion located in the crotch region 40, a second portion located in a portion of the second portion 152 of the front region 20, and a third portion located in a portion of the second portion 162 of the back region 30. In such embodiments, the second portion of the absorbent core 56 located in the second portion 152 of the front region 20 can be in an overlapping configuration with a portion of the elastic material 134 in the second portion 152 of the front region 20 and the third portion of the absorbent core 56 located in the second portion 162 of the back region 40 can be in an overlapping configuration with a portion of the elastic material 144 in the second portion 162 of the back region 40.

The overlapping configuration within the front region 20 of the second portion of the absorbent core 56 and the elastic material 134 within the front region 20 defines a front overlap region 170. The overlapping configuration within the back region 30 of the third portion of the absorbent core 56 and the elastic material 144 within the back region 30 defines a back overlap region 180. An overlap region, 170 and/or 180, in the front region 20 and/or the back region 30 has a dimension of the smallest square or rectangle that encompasses the overlap of the absorbent core 56 and the elastic material, 134 and/or 144, of the elastomeric panels, 130 and/or 140. For example, if the respective portion of the absorbent core 56 within the overlap region has a square or rectangle perimeter shape, the overlap region is defined just at the edge of the absorbent core. As another example, if the respective portion of the absorbent core 56 within the overlap region has curved perimeter shape, the overlap region is defined as the smallest square or rectangle that encompasses the curved absorbent core 56. In such an example, the overlap region may incorporate into its region a portion of the elastic material within the elastomeric panel that is not in an overlap configuration with the absorbent core.

The overlapping configuration within the front region 20 of the second portion of the absorbent core 56 and the elastic material 134 within the front region 20 defines a front overlap region 170. The elastic material 134 forming the elastomeric panel 130 of the front region 20 is elastomeric within the front overlap region 170 of the front region 20 in that it can be elongated by at least 50 percent of its relaxed length and which will recover, upon release of the applied force, at least 50 percent of its elongation. The elastic material 134 in the front overlap region 170 remains, therefore, active and capable of stretching/retracting continuously in the transverse direction (Y).

The overlapping configuration within the back region 30 of the third portion of the absorbent core 56 and the elastic material 144 within the back region 30 defines a back overlap region 180. Within the back overlap region 180 of the back region 30, the elastic material 144 is non-elastomeric wherein it is non-extensible, or if it is extensible will recover no more than 20% of its elongated length after release of an applied elongating force in a first non-extensible region 210 having a first width 200 and a first length 202 dimension as well as in a second non-extensible region 212 having a second width 204 and a second length 206 dimension. The elastic material 144 that is non-elastomeric is illustrated as the shaded regions of the back overlap region 180. The first non-extensible region 210 can have a width 200 which can be the same width dimension of the back overlap region 180. The first non-extensible region 210 can have a length 202 which can be 50% or less of the length dimension of the back overlap region 180. The second non-extensible region 212 can have a width 204 which is 50% or less than the width of the back overlap region 180 and can have a length 206 which is 50% or less than the length of the back overlap region 180. The first non-extensible region 210 and the second non-extensible region 212 can be adjacent to each other with the first non-extensible region 210 positioned closer to the back waist edge 32 of the absorbent article 10. The second non-extensible region 212 can be positioned such that it is symmetrically positioned along the width of the back overlap region 180 wherein extensible elastic material 144 of the elastomeric panel 140 located within the back overlap region 180 is positioned on either side of the second non-elastomeric region 212 in the transverse direction (Y). Thus, in such an embodiment, the first non-extensible region 210 and the second non-extensible region 212 can be positioned so as to form a "T". Non-extensible refers to a material that cannot stretch or extend by more than 25% of its relaxed length without fracture upon application of a biasing force. The elastic material 144 which is non-elastomeric in the back overlap region 180 can be rendered non-elastomeric by deactivating the elastic properties of that portion of the elastic material 144 forming the elastomeric panel 140 of the back region 30. Deactivation can be accomplished by a variety of methods. In various embodiments, a form of energy can be applied to deactivate the elastic material located within the back overlap region 180 such as, for example, pressure, heat, ultrasonic energy, combinations thereof, or the like. Deactivation can also be accomplished by severing the elastic material 144 into multiple pieces in order to render it discontinuous. Wearers of absorbent articles 10 such as described herein have body shapes in a variety of sizes, shapes, and curvature, and are generally not symmetrical. For example, some areas of the body such as the buttocks may have a larger circumference than other areas of the body such as the lower hip and/or around the legs. As described herein, when the absorbent article narrowest width 10 is positioned between the legs of the wearer a greater proportion of the absorbent article 10 is positioned on the posterior side of the wearer's body providing for better coverage of the buttocks of the wearer of the absorbent article 10. However, such coverage can be compromised if the elastic material 144 within the back region 30 were to remain fully elastomeric as the elastic material 144 can cause the back region 30 to bunch up thereby reducing the coverage of the buttocks of the wearer. The second portion of the absorbent core 56 which is in an overlapping configuration with the elastomeric panel 140 of the back region 30 can also increase the overall thickness dimension in the depth direction (Z) of the absorbent article 10 and a wearer may experience discomfort while wearing the absorbent article 10. As described herein, therefore, it is desirable to selectively deactivate a portion of the elastic material within the absorbent article 10 such as the elastic material 144 located within the back overlap region 180 of the back region 30. Deactivating this portion of the elastic material 144 can release the tension being applied to the absorbent core 56 located within the back overlap region 180 and can prevent the absorbent core 56 from bunching up within the back overlap region 180. Such deactivation can result in maintaining coverage of the back region 30 over the buttocks of the wearer as well as reducing tension discomfort that the wearer may otherwise have experienced.

Figure 5:
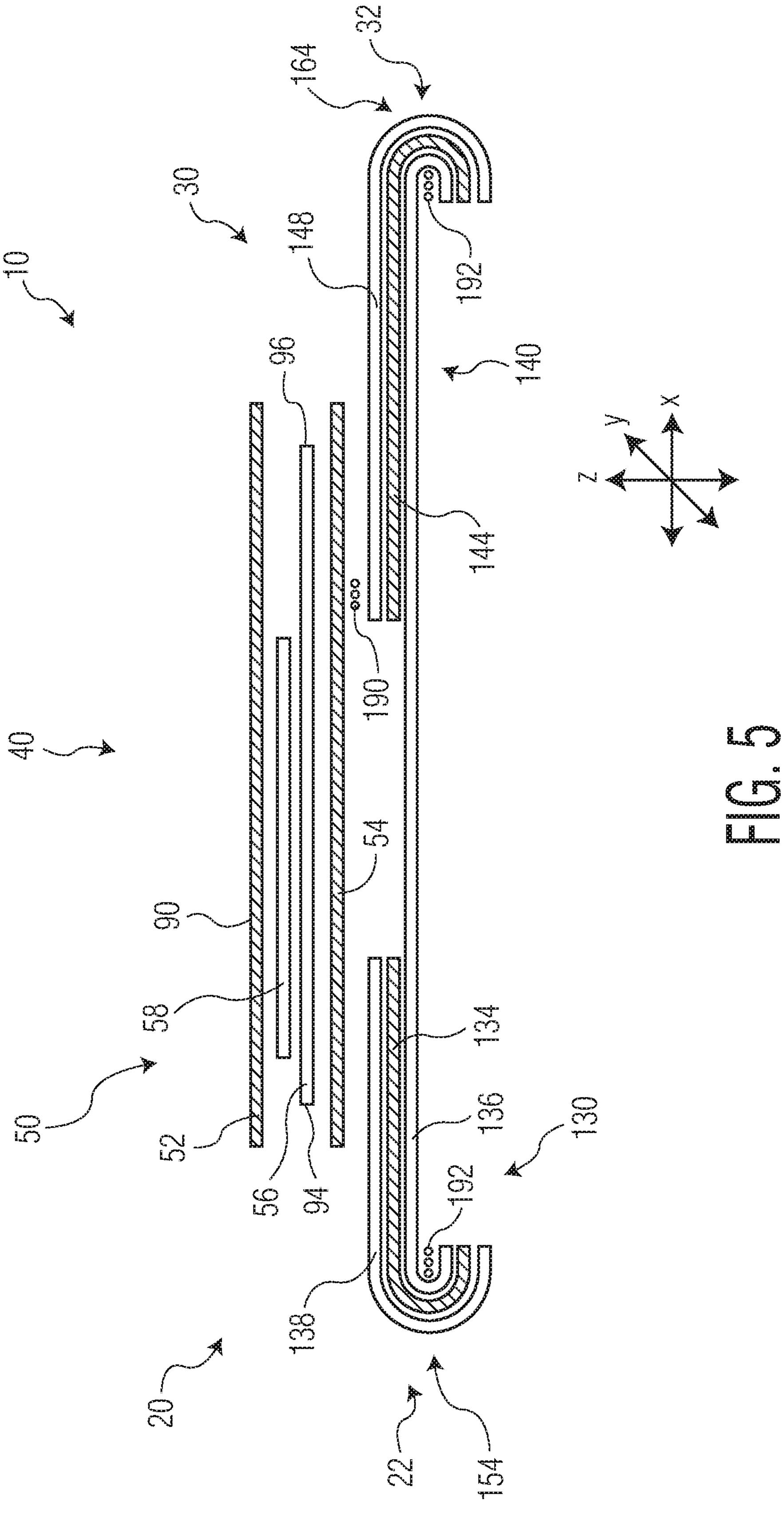
FIG. 5 is an illustration of a cross-sectional view of an alternate embodiment of the absorbent article of FIG. 3 taken along line 5-5.
Figure 6:
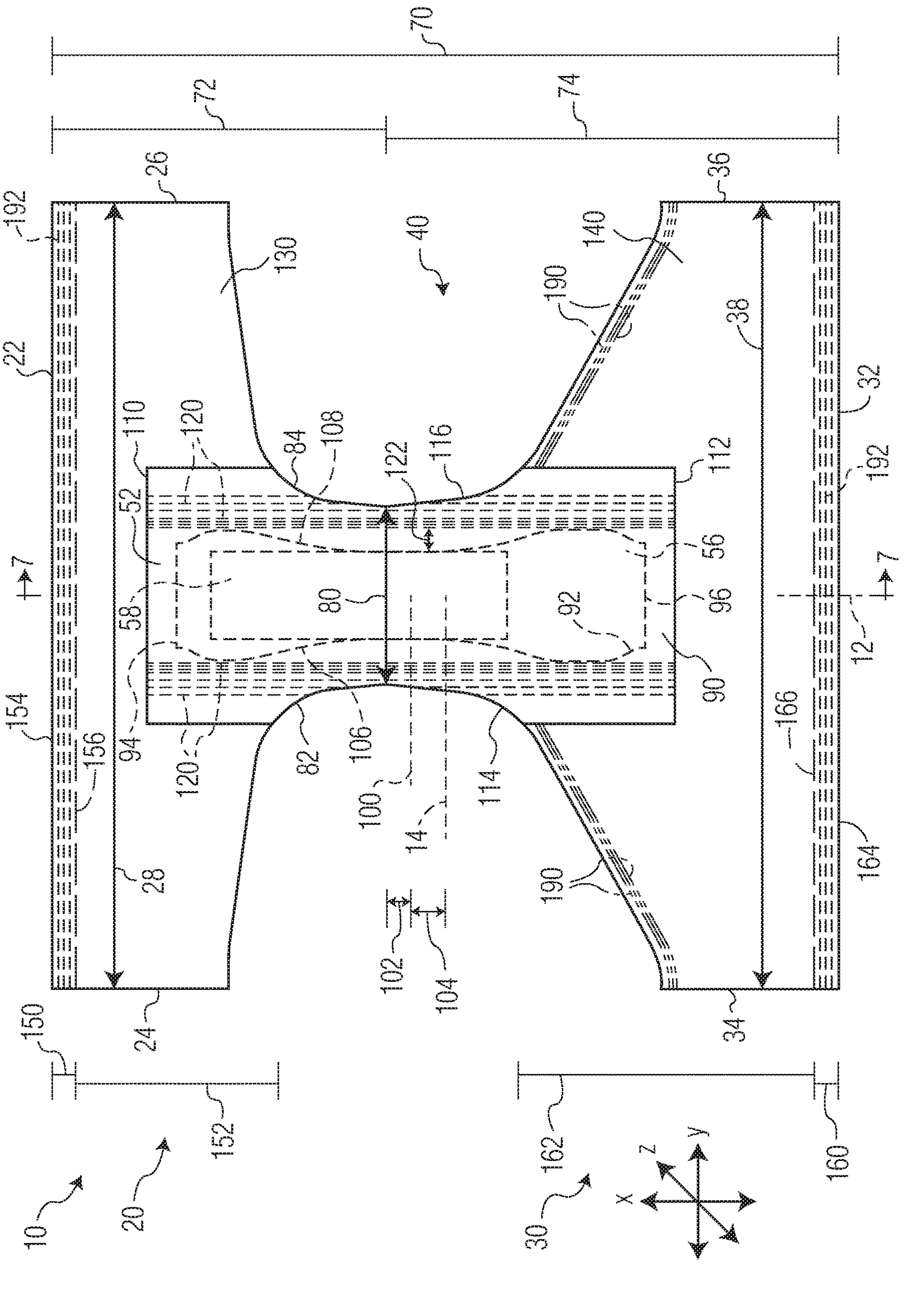
FIG. 6 is an illustration of a plan view of an alternate embodiment of an absorbent article in a longitudinally and transversely stretched and laid-flat configuration prior to the joining of the front and back regions with the surface of the absorbent article that faces the wearer when the absorbent article is worn facing the viewer.
Figure 7:
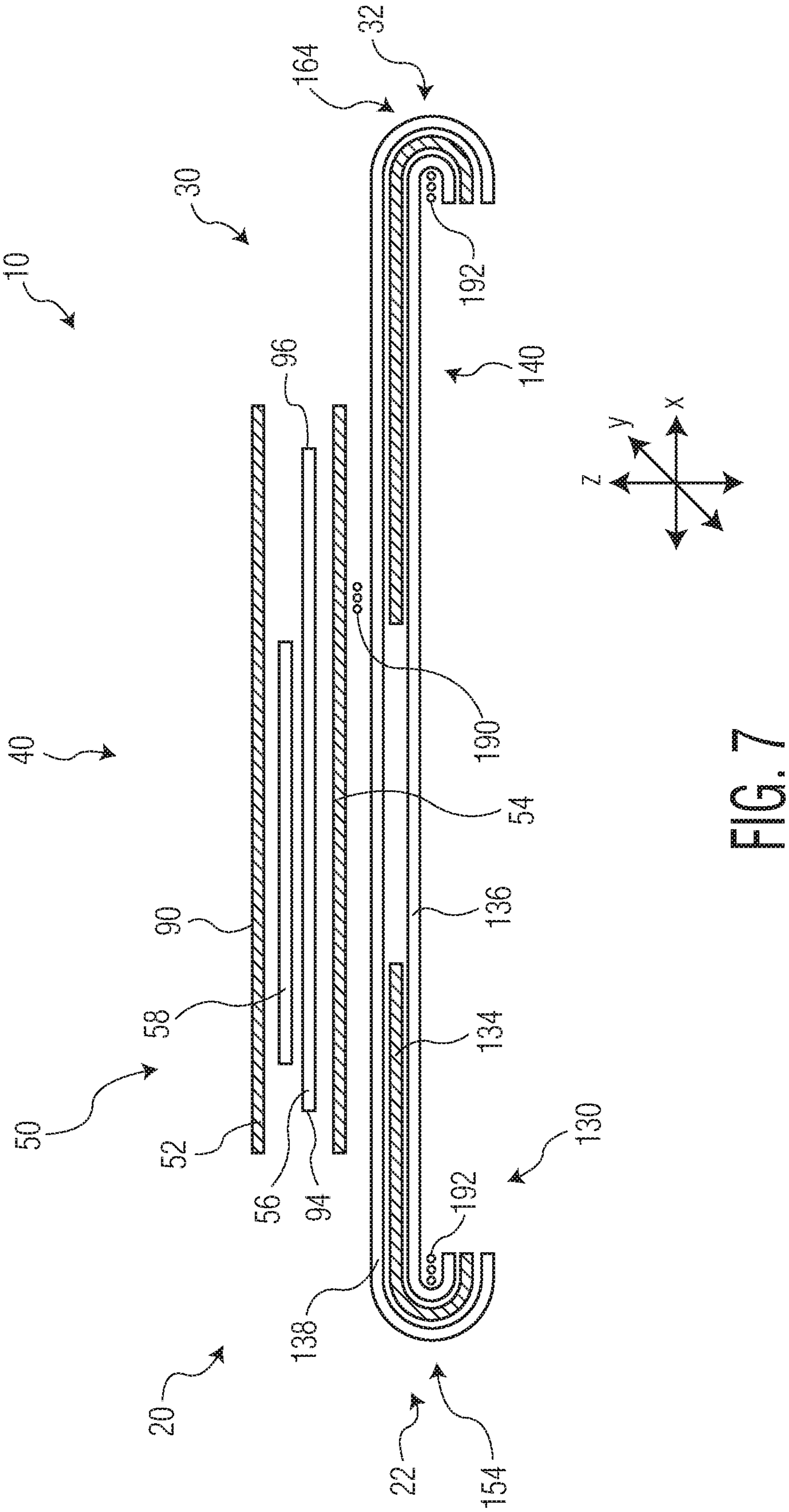
FIG. 7 is an illustration of a cross-sectional view of an embodiment of the absorbent article of FIG. 6 taken along line 7-7.

Referring to FIGS. 5-7, in various embodiments, the front region 20 and the back region 30 can be connected to each other via at least one of the materials forming the elastomeric panels, 130 and 140, respectively, of the front region 20 and the back region 30, respectively. FIG. 5 provides an exemplary illustration in which one of the nonwoven layers, such as nonwoven layer 136 is common to both elastomeric panels, 130 and 140, of each of the front region 20 and back region 30, respectively, and longitudinally extends from the front region 20, through the crotch region 40, and to the back region 30. FIGS. 6 and 7 provide an exemplary illustration of an absorbent article 10 in which both of the nonwoven layers, 136 and 138, are common to each of the elastomeric panels, 130 and 140, of the front region 20 and back region 30 and longitudinally extend from the front region 20, through the crotch region 40, and to the back region 30.

In various embodiments, the back region 30 can further have a leg elastic 190. In various embodiments, the back region 30 can have 1, 2, 3, 4, or 5 leg elastics 190. Each leg elastic 190 can be a single strand, ribbon, or strip of elastomeric material. For example, the back region 30 illustrated in FIG. 3 illustrates three strands of leg elastics 190.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:

a. a longitudinal direction and a transverse direction;

b. a longitudinal axis and a transverse axis;

c. a front region comprising a front waist edge, a first longitudinal direction side edge, a second longitudinal direction side edge transversely opposed to the first longitudinal direction side edge, a front region elastomeric panel comprising a first elastic material positioned between a first nonwoven material and a second nonwoven material;

d. a back region comprising a back waist edge, a third longitudinal direction side edge, a fourth longitudinal direction side edge transversely opposed to the third longitudinal direction side edge, a back region elastomeric panel comprising a second elastic material positioned between a third nonwoven material and a fourth nonwoven material;

e. a first side seam formed by bonding the first longitudinal direction side edge of the front region to the third longitudinal direction side edge of the back region and a second side seam formed by bonding the second longitudinal direction side edge of the front region to the fourth longitudinal direction side edge of the back region;

f. a crotch region located between the front region and the back region and interconnecting the front region and the back region;

g. an article length measured from the front waist edge to the back waist edge;

h. an absorbent core wherein a first portion of the absorbent core is located in the crotch region, a second portion of the absorbent core is located in a portion of the front region wherein the second portion of the absorbent core is in an overlapping configuration with a portion of the first elastic material and defining a front overlap region wherein the first elastic material located in the front overlap region is elastomeric in the transverse direction, and a third portion of the absorbent core is located in a portion of the back region wherein the third portion of the absorbent core is in an overlapping configuration with a portion of the second elastic material and defining a back overlap region wherein a first portion of the second elastic material located in the back overlap region is non-elastomeric in the transverse direction and defines a first non-elastomeric region having a first length dimension and a first width dimension and a second portion of the second elastic material located in the back overlap region is non-elastomeric in the transverse direction and defines a second non-elastomeric region having a second length dimension and a second width dimension wherein the second width dimension of the second non-elastomeric region is less than the first width dimension of the first non-elastomeric region;

i. an absorbent article narrowest width in the transverse direction positioned in the crotch region and between the transverse axis and the front waist edge; and j. a first article sub-length measured from the front waist edge to the absorbent article narrowest width and a second article sub-length measured from the back waist edge to the absorbent article narrowest width wherein the first article sub-length is less than the second article sub-length, wherein the first article sub-length is less than 45% of the article length and the second article sub-length is greater than 55% of the article length.

2. The absorbent article of claim 1 wherein the first elastic material and the second elastic material is a plurality of elastomeric strands.

3. The absorbent article of claim 1 wherein the first elastic material and the second elastic material is a polymeric film sheet.

4. The absorbent article of claim 1 further comprising a front region width in the transverse direction from the first longitudinal direction side edge to the second longitudinal direction side edge wherein the absorbent article narrowest width is less than 25% of the front region width.

5. The absorbent article of claim 1 wherein the absorbent core further comprises an absorbent core midpoint which is positioned between the absorbent article narrowest width and the transverse axis.

6. The absorbent article of claim 5 wherein the absorbent core midpoint is offset in the longitudinal direction from the absorbent article narrowest width by a distance from 1% to 5% of the article length.

7. The absorbent article of claim 5 wherein the absorbent article midpoint is offset in the longitudinal direction from the transverse axis by a distance from 6% to 15% of the article length.

8. The absorbent article of claim 1 wherein the back region further comprises a leg elastic.

9. The absorbent article of claim 4 further comprising a first longitudinally extending elastic material located in the crotch region of the absorbent article and separated from the absorbent core in the transverse direction at the location of each of the absorbent article narrowest width and the transverse axis by a spatial distance of at least 1.5% of the front region width.

10. The absorbent article of claim 9 further comprising a second longitudinally extending elastic material located in the crotch region of the absorbent article and separated from the absorbent core in the transverse direction at the location of each of the absorbent article narrowest width and the transverse axis by a spatial distance of at least 1.5% of the front region width.

11. An absorbent article comprising:

a longitudinal direction and a transverse direction;

a longitudinal axis and a transverse axis;

a front region comprising a front waist edge, a first longitudinal direction side edge, a second longitudinal direction side edge transversely opposed to the first longitudinal direction side edge, a front region elastomeric panel comprising a first elastic material positioned between a first nonwoven material and a second nonwoven material;

a back region comprising a back waist edge, a third longitudinal direction side edge, a fourth longitudinal direction side edge transversely opposed to the third longitudinal direction side edge, a back region elastomeric panel comprising a second elastic material positioned between a third nonwoven material and a fourth nonwoven material;

a first side seam formed by bonding the first longitudinal direction side edge of the front region to the third longitudinal direction side edge of the back region and a second side seam formed by bonding the second longitudinal direction side edge of the front region to the fourth longitudinal direction side edge of the back region;

a crotch region located between the front region and the back region and interconnecting the front region and the back region;

an article length measured from the front waist edge to the back waist edge; and an absorbent core wherein:

a first portion of the absorbent core is located in the crotch region, a second portion of the absorbent core is located in a portion of the front region wherein the second portion of the absorbent core is in an overlapping configuration with a portion of the first elastic material and defining a front overlap region wherein the first elastic material located in the front overlap region is elastomeric in the transverse direction, and a third portion of the absorbent core is located in a portion of the back region wherein the third portion of the absorbent core is in an overlapping configuration with a portion of the second elastic material and defining a back overlap region, wherein a first portion of the second elastic material located in the back overlap region is non-elastomeric in the transverse direction and defines a first non-elastomeric region having a first length dimension and a first width dimension, and a second portion of the second elastic material located in the back overlap region is non-elastomeric in the transverse direction and defines a second non-elastomeric region having a second length dimension and a second width dimension, wherein the second width dimension of the second non-elastomeric region is less than the first width dimension of the first non-elastomeric region;

an absorbent article narrowest width in the transverse direction positioned in the crotch region and between the transverse axis and the front waist edge; and wherein the first non-elastomeric region is positioned closer to the back waist edge than the second non-elastomeric region.

12. The absorbent article of claim 11 wherein the first non-elastomeric region is adjacent to the second non-elastomeric region.

13. The absorbent article of claim 11 wherein the second non-elastomeric region is symmetrically positioned along the transverse direction of the back overlap region.

14. The absorbent article of claim 11, wherein the first width dimension is equal to or greater than a maximum width dimension of the absorbent core in the rear overlap region.

15. The absorbent article of claim 11, wherein the second non-elastomeric region is disposed symmetrically between side edges of the first non-elastomeric region.

16. The absorbent article of claim 11, wherein the first length dimension of the first non-elastomeric region is between 0% and 50% of a total length dimension of the back overlap region.

17. The absorbent article of claim 11, wherein the back region further comprises a leg elastic which extends through the back region on either side of the back overlap region.

* * * * *